United States Patent [19]

Asano et al.

[11] Patent Number: 5,392,634
[45] Date of Patent: Feb. 28, 1995

[54] HYDROCARBON ANALYZER AND METHOD OF ANALYZING HYDROCARBON

[75] Inventors: Ichiro Asano; Kenji Takeda; Tsutomu Oie; Hideki Koike, all of Miyanohigashi, Japan

[73] Assignee: Horiba, Ltd., Japan

[21] Appl. No.: 112,422

[22] Filed: Aug. 24, 1993

[30] Foreign Application Priority Data

Aug. 27, 1992 [JP] Japan ............................ 4-066346[U]
Sep. 9, 1992 [JP] Japan ................................ 4-268216

[51] Int. Cl.$^6$ ............................................ G01N 30/40
[52] U.S. Cl. ........................................ 73/23.42; 422/89
[58] Field of Search ................. 73/23.42, 23.41, 23.40; 422/89

[56] References Cited

U.S. PATENT DOCUMENTS

| | | | |
|---|---|---|---|
| 3,112,639 | 12/1963 | Maxwell | 73/23.42 |
| 3,206,968 | 9/1965 | Leggoe et al. | 73/23.42 X |
| 3,444,722 | 5/1969 | Roof | 73/23.42 |
| 4,521,225 | 6/1985 | Jenkins et al. | 73/23.42 X |

FOREIGN PATENT DOCUMENTS 1236937 6/1971 United Kingdom ............... 73/23.42

*Primary Examiner*—Hezron E. Williams
*Assistant Examiner*—Joseph W. Roskos
*Attorney, Agent, or Firm*—Poms, Smith, Lande & Rose

[57] ABSTRACT

A hydrocarbon analyzer for rapidly measuring both methane and nonmethane hydrocarbons is provided. The analyzer includes a nonmethane hydrocarbon absorbing first column connected in series with a methane absorbing second column. A sample gas is propelled in a carrier gas through a carrier gas line into the first and second columns via a change-over valve for switching between a branched line severably connected between the carrier gas line and a first flame ionization detector for measuring nonmethane hydrocarbons and a second flame ionization detector connected to the second column for measuring methane. The change-over valve switches from a gas sample introducing position to a backflush position so that the sample gas is introduced into the first nonmethane hydrocarbon absorbing column where the nonmethane hydrocarbons are absorbed and the methane is transferred to the second methane absorbing column prior to backflushing the carrier gas to elute the absorbed hydrocarbons which are directed to the first and second hydrogen flame ionization detectors.

18 Claims, 7 Drawing Sheets

HYDROCARBON ANALYZER AND METHOD OF ANALYZING HYDROCARBON

BACKGROUND OF THE INVENTION

1. Field of the Invention

The present invention relates to a hydrocarbon analyzer and a method of analyzing hydrocarbons, in particular to a hydrocarbon analyzer and a method of analyzing hydrocarbons in which an exhaust gas from vehicles and other sample gases are transferred to a column with a carrier gas and methane or nonmethane hydrocarbons separated in said column are measured.

2. Description of the Prior Art

Analyzers, in which components of a sample gas, such as an exhaust gas from vehicles, are separated by a column and methane and nonmethane hydrocarbons are measured, as shown in, for example, FIGS. 10 to 13, have been known. Referring to FIGS. 10 to 13, reference numeral 1 designates a 10-way change-over valve with which a carrier gas line 2, a sample gas line 3, a sample gas-discharging line 4, a measuring pipe 5, a first adsorption column 6 and a second adsorption column 7 are connected, respectively. Reference numeral 8 designates a branched line branched from said carrier gas line 2 to be connected with said 10-way change-over valve 1, reference numeral 9a designating a by-pass line branched from the downstream side of said second column 7 to be connected with the 10-way change-over valve 1, reference numeral 10 designating a hydrogen flame ionization detector connected with the downstream side of the second column 7, and reference numeral 11 designating a resistance connected with said branched line 8 set so as to be almost equal to the total of a resistance of said first column 6 and a resistance of the second column 7.

Figure 10:
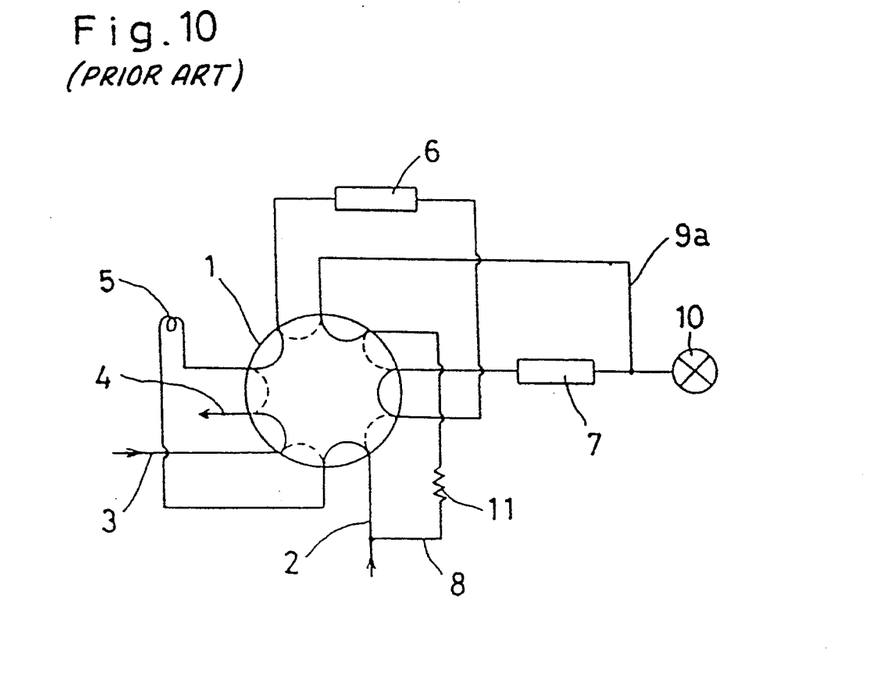
FIG. 10 is a whole block diagram showing the prior art conventional example.

By means of the 10-way change-over valve 1, the carrier gas line 2 can be connected with (and separated from) the upstream side of measuring pipe and the downstream side of first column 6, said sample gas line 3 with sample gas-discharging line 4 and the upstream side of the measuring pipe 5, the downstream side of the measuring pipe 5 with the upstream side of the first column 6 and the sample gas-discharging line 4, by-pass line 9a with the branched line 8 and the upstream side of the first column 6, and the upstream side of the second column 7 with the downstream side of the first column 6 and the branched line 8.

Figure 11:
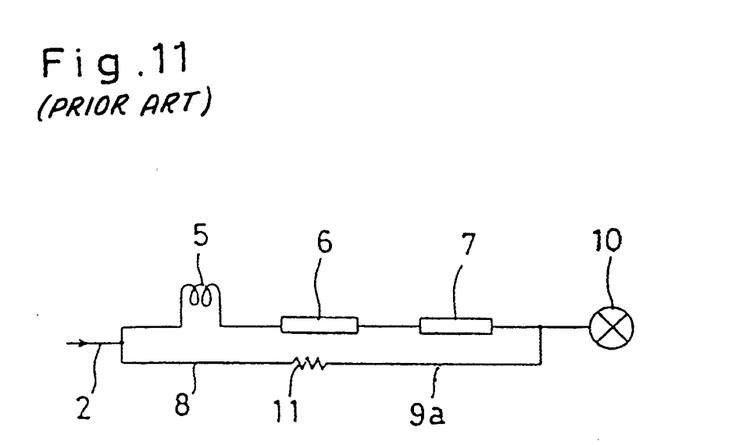
FIG. 11 is a schematic diagram showing a separation of components contained in a sample gas in the conventional example.
Figure 12:
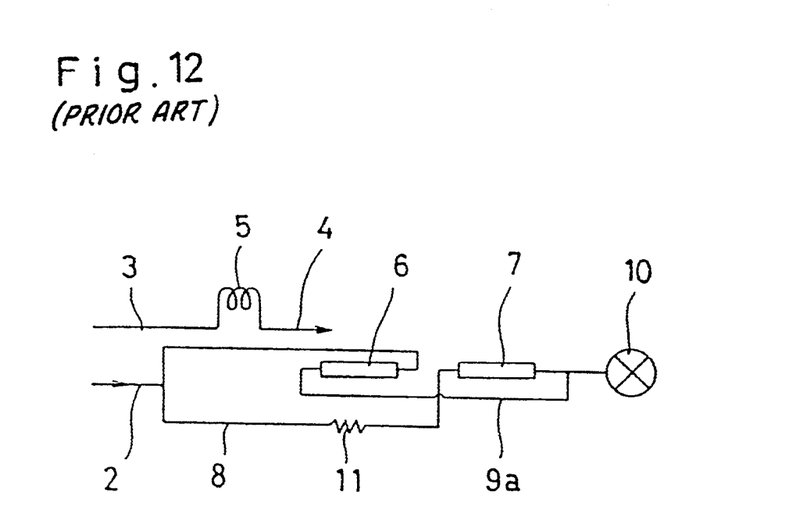
FIG. 12 is a schematic diagram showing a backflushing with a carrier gas in the conventional example.

In the above-described analyzer, when the 10-way change-over valve 1 is changed over as shown by a full line, a schematic diagram is as shown in FIG. 11. The measuring pipe 5, the first column 6, the second column 7 and said hydrogen flame ionization detector 10 are connected with the carrier gas line 2 in the order described while the branched line 8 is connected with the by-pass line 9a. When the 10-way change-over valve 1 is changed over as shown by a broken line, a schematic diagram is as shown in FIG. 12. The measuring pipe 5 is separated from the carrier gas line 2, the sample gas line 3 being connected with measuring pipe 5, and the downstream side of the measuring pipe 5 being connected with the sample gas-discharging line 4, so that an appointed quantity of sample gas introduced into the sample gas line 3 may be stored in the measuring pipe 5 while the carrier gas line 2 is connected with the downstream side of the first column 6, the by-pass line 9a being connected with the upstream side of the first column 6, and the branched line 8 being connected with the upstream side of the second column 7. In order to measure methane and nonmethane hydrocarbons, a line shown in FIG. 11 is constructed under the condition that the 10-way change-over valve 1 is changed over as shown by the full line so that the sample gas stored in the measuring pipe 5 may flow from the first column 6 to the second column 7 by a carrier gas in the carrier gas line 2. The respective components of the sample gas are repeatedly adsorbed-desorbed during the passage of the sample gas through the first column 6, but differences are produced in time from a point of time when they are adsorbed by the first column 6 due to differences in molecular weight of the respective components and the like, so that oxygen and methane are desorbed faster and eluted from the first column 6 faster to be transferred to the second column 7. On the other hand, elution times of nonmethane hydrocarbons are comparatively long, so that they are adsorbed by the first column 6 to be left in the first column 6.

Figure 13:
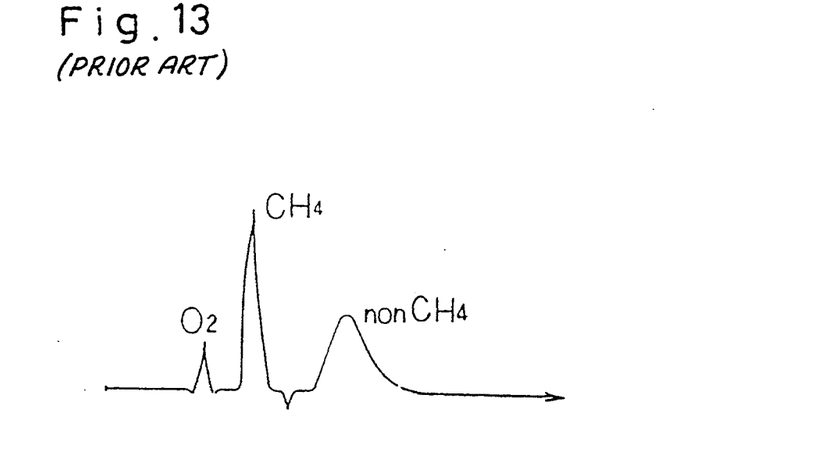
FIG. 13 is a chromatogram of the conventional prior art example.

Oxygen and methane transferred to the second column 7 are desorbed in the order described to be eluted from the second column 7 with an interval and then transferred to the hydrogen flame ionization detector 10, so that the hydrogen flame ionization detector 10 detects oxygen and methane in turn to put detected signals in a recorder (not shown). $O_2$ (oxygen) and $CH_4$ (methane) appear on a chromatogram, as shown in FIG. 13, on the basis of the respective signals put in, so that oxygen and methane are separately measured on the basis of peaks appearing on the chromatogram.

After measuring oxygen and methane in the above-described manner, the 10-way change-over valve 1 is changed over as shown by the broken line to construct a line shown in FIG. 12. In this line, the carrier gas in the carrier gas line 2 is backflushed through the first column 6 from the downstream side to the upstream side to elute the nonmethane hydrocarbons from the first column 6, followed by being transferred to the hydrogen flame ionization detector 10, thus expressing the non-$CH_4$ (nonmethane hydrocarbons) with an interval after $CH_4$, as shown in a chromatogram in FIG. 13, so that the nonmethane hydrocarbons are measured on the basis of a peak of the non-$CH_4$.

Figure 3:
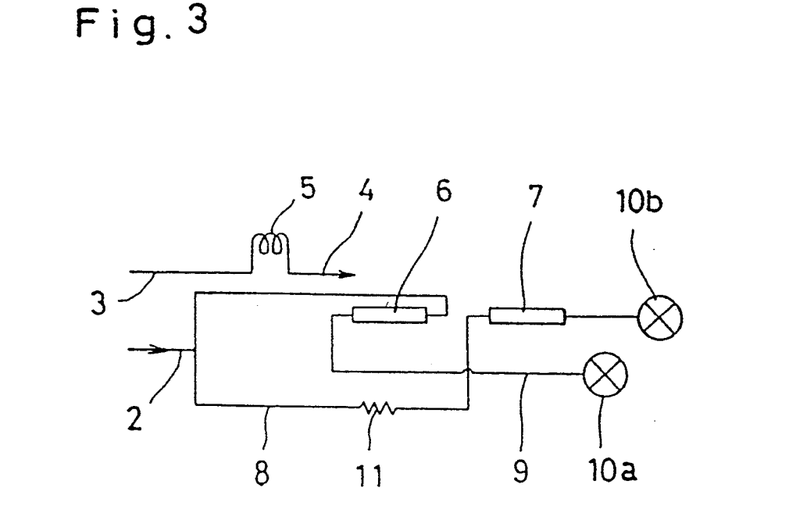
FIG. 3 is a schematic diagram showing a backflushing with a carrier gas in the first preferred embodiment.

Consequently, in the conventional analyzer, at first oxygen and methane are measured with an interval, as shown in FIG. 3, and then the carrier gas is backflushed from the downstream side to the upstream side to transfer the nonmethane hydrocarbons within the first column to the hydrogen flame ionization detector 10 to be measured, so that a time required for measuring the respective components is prolonged. Accordingly, in the case where concentrations of the components are changed within a relatively short time, as in an exhaust gas from vehicles, problems occur in that, for example, it becomes difficult to correspond to the change of the components in concentration and thus a reliability of measurement is lowered. In addition, since methane and nonmethane hydrocarbons are detected in turn by means of one hydrogen flame ionization detector 10, a sensitivity of detection is dependent upon high concentrations of methane or the nonmethane hydrocarbons, so that a problem occurs also in that lower component concentration results in reduced accuracy of measurement.

Figure 14:
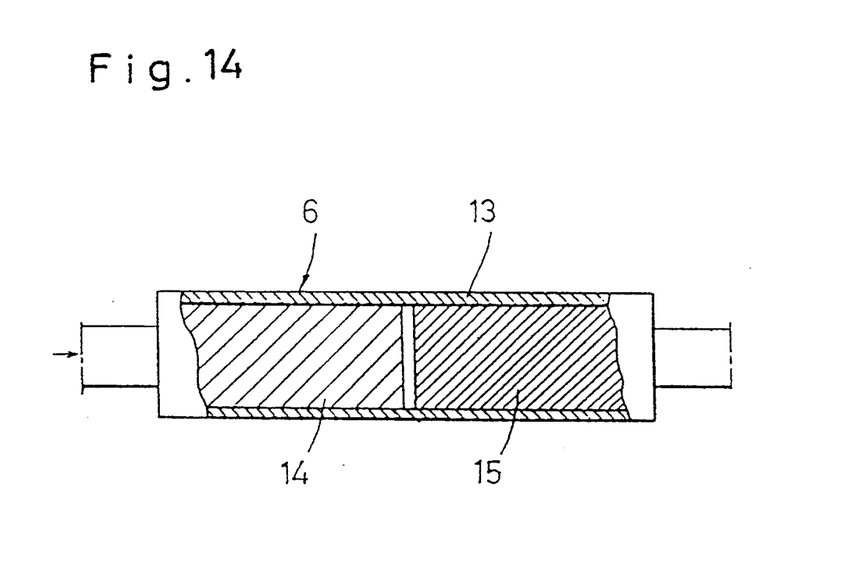
FIG. 14 is a block diagram showing the principal parts of a column in the conventional prior art example.

On the other hand, in view of the fact that the nonmethane hydrocarbons are mainly measured, the first column 6 shown in FIG. 10 has a construction as shown in FIG. 14 in order to elute the high-boiling-point hydrocarbons longer in elution time faster and thus reduce their tailing when it is backflushed with the carrier gas. Referring to FIG. 14, reference numeral 13 designates a first column pipe. A front member 14 made from a carrier made of materials hardly adsorbing the components of sample gas and coated with silicone liquids having a reduced polarity is arranged on the upstream side of said first column pipe 13 and a rear member 15 made from adsorbers, or said adsorbers coated with liquids, is arranged on the downstream side of the first column pipe so that the rear member 15 made from the adsorbers may be larger than the said front member 14 in component-adsorbing power.

The front member 14 adsorbs the high-boiling-point hydrocarbons and desorbs low-boiling-point hydrocarbons. The desorbed low-boiling-point hydrocarbons are transferred to the rear member 15. The rear member 15 adsorbs the low-boiling-point hydrocarbons other than methane transferred from the front member 14 to elute methane faster, whereby methane is transferred to the second column 7. Accordingly, as above described, referring to FIG. 12, when the first column 6 is backflushed with the carrier gas, the high-boiling-point hydrocarbons adsorbed by the front member 14 having a comparatively small adsorbing power are easily eluted and introduced into the hydrogen flame ionization detector 10 as they are. In addition, the low-boiling-point hydrocarbons adsorbed by the rear member 15 are also comparatively easily eluted and transferred to the hydrogen flame ionization detector 10 within a short time, so that the nonmethane hydrocarbons within the first column 6 can be measured as one peak with reducing their tailing.

Components, such as alcohols, having an OH-group and thus high in polarity, are rarely contained in the exhaust gas from vehicles and other sample gases; and thus it has been possible to measure the nonmethane hydrocarbons contained in them with reducing their tailing by means of the conventional nonmethane hydrocarbon analyzer. However, recently fuels also containing components, such as alcohols, having an OH-group and thus high in polarity, have been used. Accordingly, if the sample gas containing the components, such as alcohols, having an OH-group and thus high in polarity, is introduced into the first column 6, as shown in FIG. 14, oxygen and methane desorbed and are eluted from the first column 6 faster during the passage of the sample gas through the first column 6 to be transferred to the second column 7.

However, the front member 14 of the first column 6 adsorbs the components having an OH-group in addition to the high-boiling-point hydrocarbons, so that the components having an OH-group are strongly adsorbed by the front member 14 to tail during the backflushing. As described above, referring to FIG. 12, when the carrier gas is backflushed from the downstream side to the upstream side of the first column 6; that is, the carrier gas is backflushed from the side of the rear member 15 to the front member 14 of the column 6, as seen in FIG. 14, the components, such as alcohols, having an OH-group and thus high in polarity, are eluted with difficulty from the front member 14; and thus it takes a longer time to pass through the front member 14, so that it takes a remarkably long time to measure the respective nonmethane hydrocarbon components. Moreover, a problem occurs in that the tailing occurs to make the measurement impossible. In short, it is impossible to measure the whole quantity of nonmethane hydrocarbons adsorbed by the column at high speed with reducing the tailing.

SUMMARY OF THE INVENTION

The present invention solves the above-described problems, and it is an object of the present invention to provide a hydrocarbon analyzer and a method of analyzing hydrocarbons capable of not only shortening a time required for measuring methane and nonmethane hydrocarbons but also accurately measuring the whole quantity of nonmethane hydrocarbons with reducing their tailing even in the case where components, such as alcohols, having an OH-group and thus high in polarity, are contained in a sample gas.

The present invention at first solves problems that when the conventional analyzer is used, as shown by the chromatogram in FIG. 13, oxygen and methane are measured at intervals and then the nonmethane hydrocarbons are measured, so that the time required for measuring the respective components is prolonged. Thus, for example, in the case where the components are changed in concentration within a comparatively short time, as in the exhaust gas from vehicles, it becomes difficult to follow the change of the components in concentration and thus the reliability of measurement is lowered and the accuracy of measurement is reduced because methane and nonmethane hydrocarbons are detected sequentially by means of one hydrogen flame ionization detector.

Thus, (1) The hydrocarbon analyzer according to the present invention, in which a first column, a second column and a second hydrogen flame ionization detector are connected in the order described to introduce a sample gas into the first column with a carrier gas within a carrier gas line, thereby adsorbing nonmethane hydrocarbons in the said sample gas by the first column and transferring methane in the sample gas to the second column where methane is separated, and subsequently, the carrier gas line is changed in connection to the downstream side of the first column and the upstream side of the second column in parallel, respectively, to backflush the carrier gas from the downstream side to the upstream side of the first column, thereby eluting the nonmethane hydrocarbons adsorbed by the first column, is characterized in that a first hydrogen flame ionization detector is connected with the upstream side of the first column during the backflushing.

In addition, according to a method of analyzing hydrocarbons of the present invention, a first column, a second column and a second hydrogen flame ionization detector are connected in the order described to introduce a sample gas into the first column with a carrier gas within a carrier gas line, thereby adsorbing nonmethane hydrocarbons in the sample gas by the first column and transferring methane in the sample gas to the second column where methane is separated, and subsequently, the carrier gas line is changed in connection to the downstream side of the first column and the upstream side of the second column separately in parallel and a first hydrogen flame ionization detector is connected with the upstream side of the first column to introduce said carrier gas into the first column and the second column simultaneously in parallel, thereby eluting methane from the second column and transferring it to the second hydrogen flame ionization detector, and the carrier gas is backflushed from the downstream side to the upstream side of the first column to elute nonmethane hydrocarbons adsorbed by the first column and transfer them to the first hydrogen flame ionization detector.

Next, the present invention solves the conventional problem that, referring to FIG. 12, when the carrier gas is backflushed from the downstream side to the upstream side of the first column 6, that is, the carrier gas is backflushed from the side of the rear member 15 to the front member 14 made from a carrier of materials hardly adsorbing the components of sample gas and coated with silicone liquids having a reduced polarity as shown in FIG. 14, the components, such as alcohols, having an OH-group and thus high in polarity, are eluted with difficulty from the front member 14. Thus it is difficult to measure the whole quantity of nonmethane hydrocarbons adsorbed by the column at high speed with reduced tailing.

Thus, (2) The hydrocarbon analyzer according to the present invention, in which a sample gas is introduced into a single column comprising a front member made from a carrier coated with liquids and a rear member made of adsorbers with a carrier gas from the side of the front member to adsorb nonmethane hydrocarbons in the sample gas by the column and separately elute components other than the nonmethane hydrocarbons from the column; and then the carrier gas is backflushed from the side of the rear member to the side of the front member of the column to elute the nonmethane hydrocarbons adsorbed by the column and transfer them to a detector where they are measured, is characterized in that the carrier constituting the front member of the column is coated with liquids having an OH-group.

In addition, a method of analyzing hydrocarbons is provided, in which a sample gas is introduced into a column comprising a front member made from a carrier coated with liquids having an OH-group and a rear member made of adsorbers with a carrier gas from the side of the front member to adsorb nonmethane hydrocarbons in the sample gas by the column and separately elute components other than the nonmethane hydrocarbons from the column; and then the carrier gas is backflushed from the side of the rear member to the side of the front member of the column to elute the nonmethane hydrocarbons adsorbed by the column and transfer them to a detector where they are measured.

(3) Furthermore, in order to measure nonmethane hydrocarbon components, such as alcohols, having an OH-group and thus high in polarity, the present invention can provide a hydrocarbon analyzer, in which a sample gas is introduced into a column comprising a front member made from a carrier coated with liquids and a rear member made of adsorbers with a carrier gas from the side of the front member to adsorb the nonmethane hydrocarbons in the sample gas by the column and separately elute components other than nonmethane hydrocarbons from the column and then the carrier gas is backflushed from the side of the rear member to the side of the front member of the column to elute the nonmethane hydrocarbons adsorbed by the column and transfer them to a detector where they are measured, characterized in that a middle member is provided between the front member and the rear member, the carrier constituting the front member being coated with the liquids having an OH-group, a carrier constituting the middle member being coated with silicone liquids, and the column comprising the front member, the middle member and the rear member arranged in the order described.

Concurrently, a method of analyzing hydrocarbons is provided, in which a sample gas is introduced into a column comprising a front member made from a carrier coated with liquids having an OH-group, a middle member made from a carrier coated with silicone liquids, and a rear member made of adsorbers arranged in the order described from the side of the front member with a carrier gas to separately adsorb alcohols and aromatic hydrocarbons in the sample gas by the front member, high-boiling-point aliphatic hydrocarbons by the middle member, and low-boiling-point aliphatic hydrocarbons by the rear member, respectively, and separately elute components other than nonmethane hydrocarbons from the column; and then the carrier gas is backflushed from the side of the rear member to the side of the front member of the column to elute the above-described respective components adsorbed by the column and transfer them to a detector where the respective components are measured.

With the hydrocarbon analyzer according to the above (1) of the present invention, the sample gas is introduced into the first column with the carrier gas under the condition that the first column, the second column and the second hydrogen flame ionization detector are connected in the order described. This sample gas is transferred to the first column and the second column in turn, but the nonmethane hydrocarbons in the sample gas are adsorbed by the first column while methane is eluted from the first column to be transferred to the second column. The elution of methane from the first column can be known from, for example, a time after an addition of the sample gas to the carrier gas. Accordingly, after methane is eluted from the first column, the carrier gas line is connected with the downstream side of the first column and the upstream side of the second column separately in parallel, and the first hydrogen flame ionization detector is connected with the upstream side of the first column and thereafter the carrier gas is introduced into the first column and the second column in parallel, respectively.

Accordingly, methane transferred to the second column is repeatedly adsorbed by and desorbed from the second column to be eluted from the second column and transferred to the second hydrogen flame ionization detector where methane is detected. On the other hand, the first column is backflushed with the carrier gas from the downstream side to the upstream side thereof to elute the nonmethane hydrocarbons adsorbed by the first column and transfer them to the first hydrogen flame ionization detector, so that the first hydrogen flame ionization detector detects the nonmethane hydrocarbons to put out signals. That is to say, methane in the first column and the nonmethane hydrocarbons in the second column are detected by the first and second hydrogen flame ionization detectors separately in parallel in time, whereby it is possible to remarkably shorten the time required for measuring methane and the nonmethane hydrocarbons. The nonmethane hydrocarbons and methane are detected by the first and second hydrogen flame ionization detectors exclusive thereto, so that the nonmethane hydrocarbons and methane can be detected in high sensitivity.

In the hydrocarbon analyzer (2) of the present invention, the front member of the column is made of a carrier coated with liquids having an OH-group. Accordingly, in the case where the components such as alcohols, having an OH-group and thus high in polarity, are also contained in the sample gas introduced into the column with the carrier gas, the components such as alcohols, and the high-boiling-point hydrocarbons are adsorbed by the front member while the low-boiling-point hydrocarbons are transferred to the rear member. The adsorbing power for the components, such as alcohols, and the high-boiling-point hydrocarbons of the front member is smaller than that of the rear member. The low-boiling-point hydrocarbons other than methane are adsorbed by the rear member and other components, such as methane, are eluted from the column faster to be transferred to the downstream side.

Accordingly, when the carrier gas is backflushed from the side of the rear member to the side of the front member of the column, the components, such as alcohols, and the high-boiling-point hydrocarbons can be easily eluted from the front member and the components eluted from the front member are transferred to the detector as they are, so that the components adsorbed by the front member can be introduced into the detector within a short time. In addition, the components adsorbed by the rear member are the low-boiling-point hydrocarbons other than methane, and these also can be comparatively easily eluted quickly to be transferred to the detector, so that the whole quantity of the nonmethane hydrocarbons adsorbed by the column can be measured in high speed with reduced tailing.

Furthermore, with the hydrocarbon analyzer (3) of the present invention, in the case where the column comprises the front member, the middle member and the rear member, alcohols and the aromatic hydrocarbons contained in the sample gas are adsorbed by the front member, the high-boiling-point aliphatic hydrocarbons contained in the sample gas being adsorbed by the middle member, and the low-boiling-point aliphatic hydrocarbons contained in the sample gas being adsorbed by the rear member. Accordingly, also in the case where the high-boiling-point aliphatic hydrocarbons are contained in the sample gas, when the carrier gas is backflushed from the side of the rear member to the side of the front member of the column, the above-described respective components can be eluted within a comparatively short time and thus the whole quantity of the nonmethane hydrocarbons adsorbed by the column can be measured in high speed with the reduced tailing.

The front member and the rear member according to the present invention can be optionally arranged; that is, both members may be integrally arranged or separately arranged side by side. Also the front member, the middle member and the rear member according to the present invention can be optionally arranged. That is, these members may be integrally arranged or separately arranged side by side. At this time, in the column, alcohols and the aromatic hydrocarbons contained in the sample gas are adsorbed by the front member, the high-boiling-point aliphatic hydrocarbons contained in the sample gas being adsorbed by the middle member, and the low-boiling-point aliphatic hydrocarbons contained in the sample gas being adsorbed by the rear member. Accordingly, this hydrocarbon analyzer is suitable for the analysis when the high-boiling-point aliphatic hydrocarbons, such as $n-C_6H_{14}$ or $n-C_7H_{16}$, are contained in the sample gas.

Materials for the carrier according to the present invention, include, for example, diatomaceous earth or fluororesins and the liquids having an OH-group to be coated on the carrier include, for example, polyethylene glycol. The adsorbers constituting the rear member include, for example, porous polymeric beads, but these adsorbers can be used not only as they are but also used in the form coated with low vapor pressure, thermally stable liquids such as Apiezon grease L or Apiezon grease M, as the rear member.

DETAILED DESCRIPTION OF THE PREFERRED EMBODIMENTS

Figure 1:
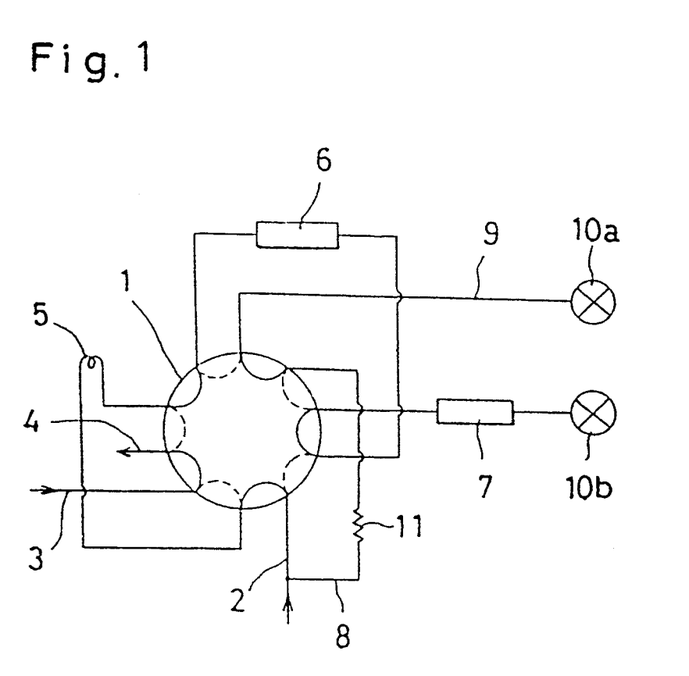
FIG. 1 is a block diagram showing a first preferred embodiment of the present invention.
Figure 2:
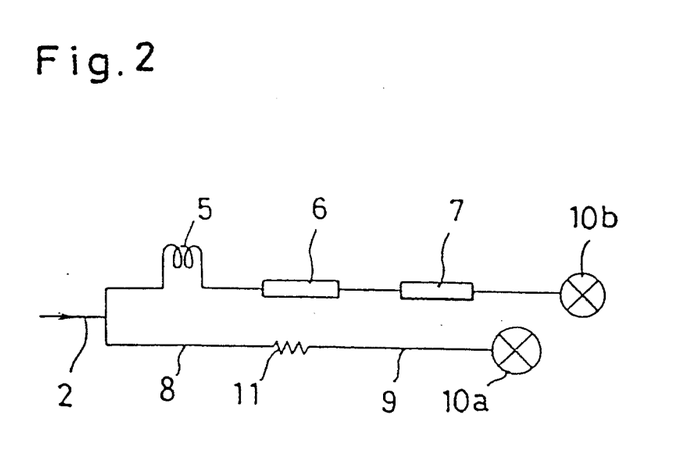
FIG. 2 is a schematic diagram showing a separation of components contained in a sample gas in said first preferred embodiment.

The first preferred embodiment of the present invention will be described below with reference to FIGS. 1 to 4. Referring to FIGS. 1 to 3, reference numerals 1 to 8 are the same as in the conventional example shown in FIG. 10, so that their detailed description is omitted. Reference numeral 9 designates a by-pass line connected with the 10-way change-over valve 1, a first hydrogen flame ionization detector 10a being connected with the by-pass line 9, and a second hydrogen flame ionization detector 10b being connected with the downstream side of the second adsorption column 7. Reference numeral 11 designates a resistance of the branched line 8 set so as to be almost equal to the total of the respective resistances of the first adsorption column 6 and the second column 7.

In the above-described analyzer, when the 10-way change-over valve 1 is changed over to an initial position as shown by a full line, a schematic diagram is as shown in FIG. 2. The measuring pipe 5, the first column 6, the second column 7 and the second hydrogen flame ionization detector 10b are connected with the carrier gas line 2 in the order described while the branched line 8 branched from the carrier gas line 2 is connected with the by-pass line 9 and the first hydrogen flame ionization detector 10a is connected with the downstream side of the by-pass line 9. When the 10-way change-over valve 1 is changed over to a backflush position as shown by a broken line, a flow sheet is as shown in FIG. 3. The measuring pipe 5 is separated from the carrier gas line 2, the sample gas line 3 being connected with the measuring pipe 5, and the downstream side of the measuring pipe 5 being connected with the sample gas-discharging line 4, so that an appointed quantity of sample gas introduced into the sample gas line 3 may be stored in the measuring pipe 5 while the carrier gas line 2 is connected with the downstream side of the first column 6 and the upstream side of the first column 6 is connected with the by-pass line 9, so that the first hydrogen flame ionization detector 10a is connected with the upstream side of the first column 6. And, the branched line 8, including resistor 11, is connected with the upstream side of the second column 7 and the second hydrogen flame ionization detector 10b is connected with the downstream side of the second column 7.

In order to measure methane and nonmethane hydrocarbons, a line shown in FIG. 2 is constructed under the condition that the 10-way change-over valve 1 is changed over as shown by the full line so that the sample gas, such as exhaust gas from vehicles, stored in the measuring pipe 5 may be flowed from the first column 6 to the second column 7 by a carrier gas in the carrier gas line 2. During the passage of the sample gas through the first column 6, oxygen and methane contained in the sample gas are eluted from the first column 6 in turn faster to be transferred to the second column 7 because their elution times are comparatively short. On the other hand, elution times of nonmethane hydrocarbons contained in the sample gas are comparatively long, so that they are adsorbed by the first column 6 to be left in the first column 6.

The elution of oxygen and methane from the first column 6 begins from the start of adding the sample gas in the measuring pipe 5 to the carrier gas and ends at the switching of the 10-way change-over valve 1 to a backflush position as shown by the broken line, thus constructing a line shown in FIG. 3. In this line, the carrier gas in the carrier gas line 2 is backflushed through the first column 6 from the downstream side to the upstream side to flow to not only the first hydrogen flame ionization detector 10a but also to the second hydrogen flame ionization detector 10b through the branched line 8, the resistance 11 and the second column 7 in parallel in time.

Figure 4A:
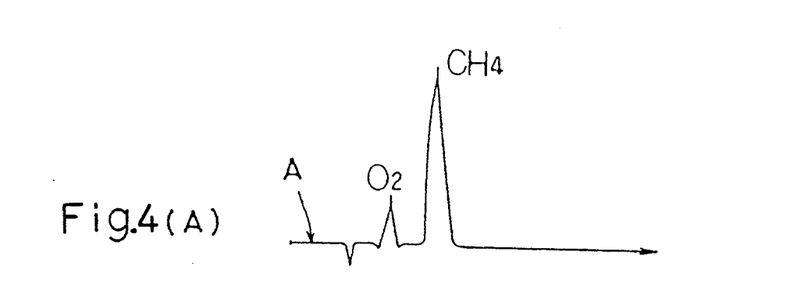
FIG. 4(A) and 4(B) are chromatograms of the first preferred embodiment.
Figure 4B:
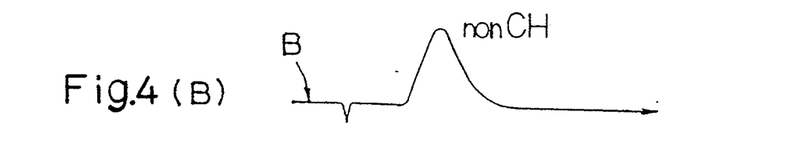
Figure 5:
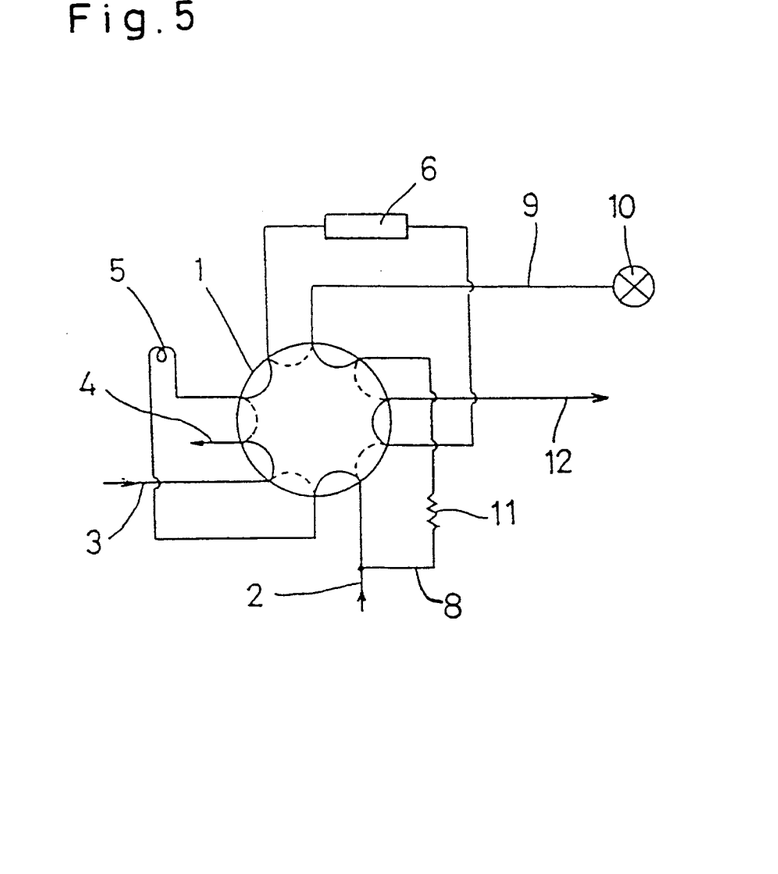
FIG. 5 is a block diagram showing a second preferred embodiment of the present invention.

Accordingly, oxygen and methane transferred by the arrangement of FIG. 2 to the second column 7 from the first column 6 are eluted in turn from the second column 7 with an interval and then transferred to the second hydrogen flame ionization detector 10b and detected, so that $O_2$ (oxygen) and $CH_4$ (methane) appear on a chromatogram A with an interval as peaks, as shown in FIG. 4(A). By a backflushing (as shown in FIG. 3) of the first column 6 made in parallel to the detection of oxygen and methane in time, the nonmethane hydrocarbons eluted from the first column 6 are detected by the first hydrogen flame ionization detector 10a, so that non-$CH_4$ (nonmethane hydrocarbons) appear on a chromatogram B as a peak in parallel to said chromatogram A in time, as shown in FIG. 4(B).

Since the measurement of oxygen and methane and the measurement of nonmethane hydrocarbons are carried out in parallel in time, the time required for measuring these components can be remarkably shortened.

Accordingly, the hydrocarbon analyzer can follow the change of the components in concentration even in the case where the concentrations of the components are rapidly changed, as in a sample gas such as exhaust gas from vehicles. In the line of the first column 6 shown in FIG. 3, merely the first column 6 is a resistance against the flow of the carrier gas. On the other hand, the resistance 11 exists in the line of the second column 7. Accordingly, a larger quantity of carrier gas flows in the line of the first column as compared with the line of the second column, and thus the first column 6 is efficiently backflushed to promote the elution of nonmethane hydrocarbons adsorbed by the first column, so that their tailing can be reduced.

As described above, in this preferred embodiment, nonmethane hydrocarbons and methane transferred by the carrier gas are divided into the first column and the second column. After these components are divided, the connection of the carrier gas line with the first column and the second column is changed to connect the second hydrogen flame ionization detector with the downstream side of the second column; and the first hydrogen flame ionization detector is connected with the upstream side of the first column under the condition that the first column is backflushed with the carrier gas. That is to say, not only can methane eluted from the second column be detected by the second hydrogen flame ionization detector, but also the nonmethane hydrocarbons eluted from the first column by the backflushing can be detected by the first hydrogen flame ionization detector simultaneously with the detection of methane in parallel in time.

Accordingly, the respective times required for measuring methane and the nonmethane hydrocarbons can be remarkably shortened as compared with the above-described conventional methane-nonmethane hydrocarbon analyzer, and thus methane and the nonmethane hydrocarbons can be measured at high speed. For example, even in the case where the sample gas is exhaust gas from vehicles of which concentrations of components are comparatively rapidly changed, the hydrocarbon analyzer, according to this preferred embodiment, can follow the change of concentration of the components, and thus the reliability of measurement can be improved. Moreover, since the nonmethane hydrocarbons and methane are measured by the respective exclusive first and second hydrogen flame ionization detectors, they can be detected in high sensitivity, regardless of the concentrations thereof to measure them in high accuracy.

A second preferred embodiment of the present invention will be described with reference to FIGS. 5 to 8. In FIGS. 5 to 8, reference numeral 6 designates a column connected with a 10-way change-over valve 1 on the upstream side and the downstream side thereof. Reference numeral 9 designates a by-pass line connected with the 10-way change-over valve 1 and a hydrogen flame ionization detector 10 is connected with the downstream side of the by-pass line 9. Reference numeral 11 designates a resistance of a branched line 8, and reference numeral 12 designates a sample gas-discharging line connected with the 10-way change-over valve 1.

Figure 6:
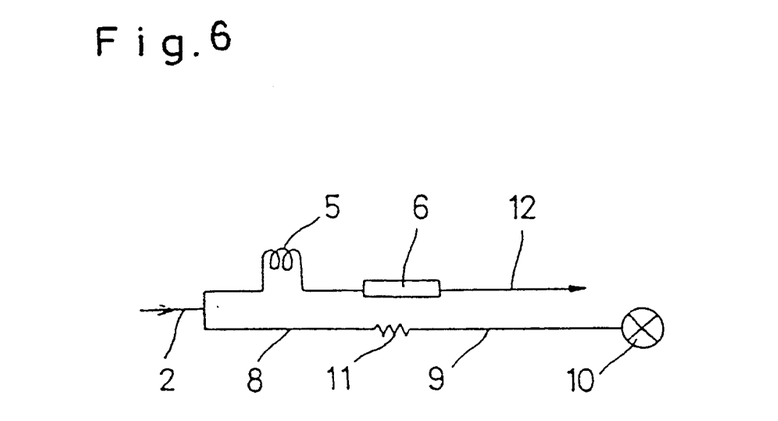
FIG. 6 is a schematic diagram showing a separation of components contained in a sample gas in said second preferred embodiment.
Figure 7:
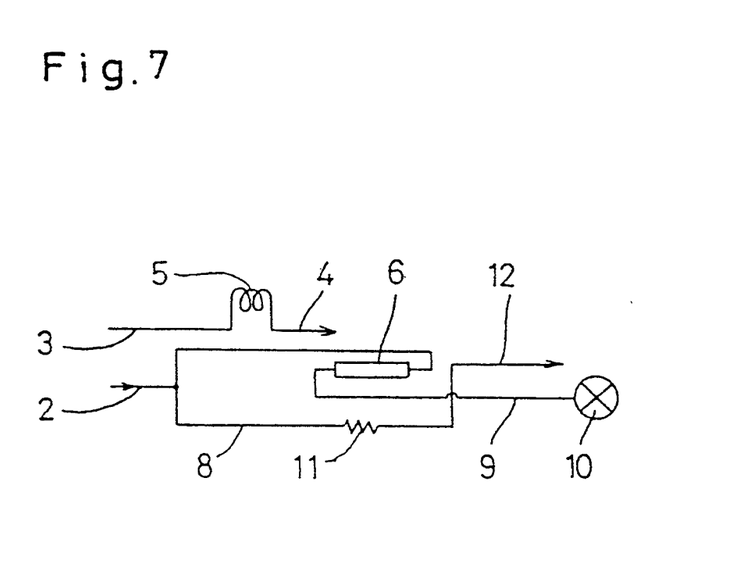
FIG. 7 is a schematic diagram showing a backflushing with a carrier gas in the second preferred embodiment.

In the above-described analyzer, when the 10-way change-over valve 1 is changed over as shown by a full line, a flow sheet is as shown in FIG. 6. The measuring pipe 5, the column 6 and the sample gas-discharging line 12 are connected with a carrier gas line 2 in the order described while the branched line 8 is connected with the by-pass line 9 and the hydrogen flame ionization detector 10 is connected with the downstream side of the by-pass line 9. When the 10-way change-over valve 1 is changed over as shown by a broken line, a flow sheet is as shown in FIG. 7. The measuring pipe 5 is separated from the carrier gas line 2, a sample gas line 3 being connected with the measuring pipe 5, and a sample gas-discharging line 4 being connected with the downstream side of the measuring pipe 5, so that an appointed quantity of sample gas introduced into the sample gas line 3 may be stored in the measuring pipe 5 while the carrier gas line 2 is connected with the downstream side of the column 6, the upstream side of the column 6 being connected with the by-pass line 9, and the sample gas-discharging line 12 being connected with the branched line 8.

Figure 8:
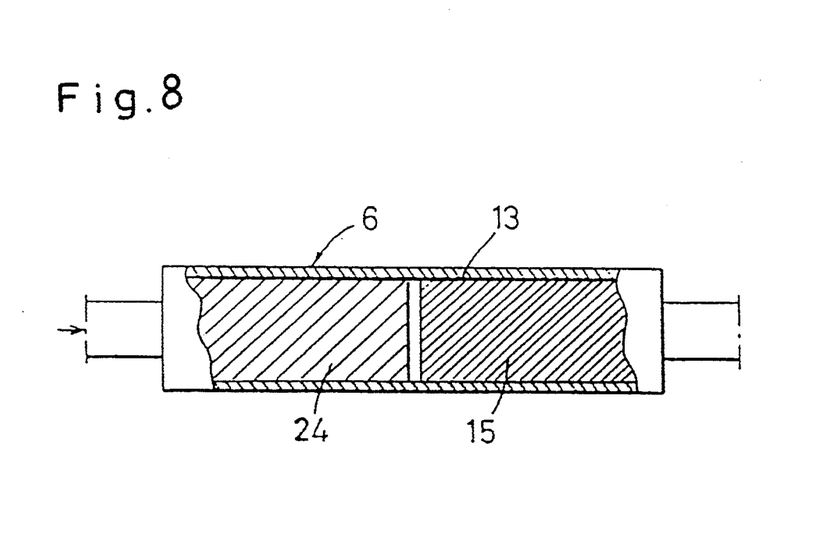
FIG. 8 is a block diagram showing the principal parts of a column in the second preferred embodiment.

The column 6 comprises a front member 24 made from a carrier made of diatomaceous earth hardly adsorbing components contained in a sample gas and coated with polyethylene glycol as liquids having an OH-group arranged on the upstream side within a column pipe 13 and a rear member is made from porous polymeric beads as adsorbers arranged on the downstream side within said column pipe 13, as shown in FIG. 8. Front member 24 adsorbs components having an OH-group and thus high in polarity and high-boiling-point hydrocarbons, while low-boiling-point hydrocarbons are fast eluted from the front member 24 to be transferred to the rear member 15. The rear member 15 adsorbs the low-boiling-point hydrocarbons other than methane and other components, such as methane, are fast eluted from the rear member 15, so that they are transferred to the downstream side. Since the rear member 15 is made of adsorbers in the above-described manner, a power adsorbing component of the rear member 15 is larger than that of the front member 24.

In order to measure nonmethane hydrocarbons, a line shown in FIG. 6 is constructed under the condition that the 10-way changeover valve 1 is changed over as shown by the full line so that the sample gas, such as exhaust gas from vehicles, containing said components, such as alcohols, having an OH-group and thus high in polarity, and stored in the measuring pipe 5, may flow from the column 6 to the sample gas-discharging line 12. During the passage of the sample gas through the column 6, the components having an OH-group and high-boiling-point hydrocarbons are adsorbed by the front member 14 while the low-boiling-point hydrocarbons are fast eluted from the front member 24 to be transferred to the rear member 15 where they are adsorbed. On the other hand, oxygen and methane, whose elution times are short, are faster eluted from the front member 24 and the rear member 15 to be discharged through the sample gas-discharging line 12.

After oxygen and methane are eluted from the column 6, as described above, the 10-way change-over valve 1 is changed over as shown by the broken line to construct a line shown in FIG. 7. In this line, the carrier gas within the carrier gas line 2 is backflushed from the downstream side to the upstream side of the column 6. At this time, the components, such as alcohols, having an OH-group and thus high in polarity, and the high-boiling-point hydrocarbons adsorbed by the front member 14 can be comparatively easily eluted from the front member 14 and transferred to the detector 10 through the by-pass line 9 as they are, so that the above-described respective components adsorbed by the front member 24 can be introduced into the detector 10 within a short time (at high speed). In addition, the components adsorbed by the rear member 15 are the low-boiling-point hydrocarbons other than methane, so that these also can be comparatively easily eluted quickly to be transferred to the detector 10. Accordingly, the nonmethane hydrocarbons adsorbed by the front member 24 and the rear member 15 of the column 6 can be measured at high speed as one peak in high accuracy with reduced tailing. In the case where the components, such as alcohols, having an OH-group and thus high in polarity, are not contained in the sample gas, the front member 24 adsorbs the high-boiling-point hydrocarbons contained in the sample gas.

Although the front member 24 and the rear member 15 are housed in one piece of column pipe 13, the front member 24 and the rear member 15 can be independently constructed, respectively, to be arranged side by side. In this preferred embodiment, oxygen and methane eluted from the column 6 are discharged through the sample gas-discharging line 12. It is, however, also possible that the column 6 comprising the front member 24 and the rear member 15 can be used as the first column in the conventional hydrocarbon analyzer shown in FIG. 10 to measure oxygen and methane together with the nonmethane hydrocarbons.

Figure 9:
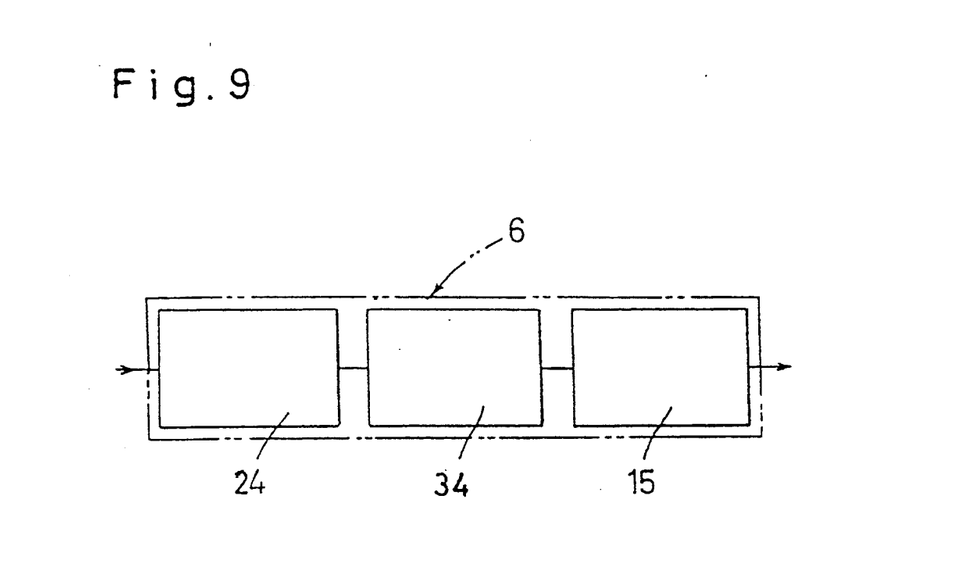
FIG. 9 is a block diagram showing the principal parts of a column in the third preferred embodiment of the present invention.

FIG. 9 shows principal parts of a third preferred embodiment and relates to the column 6. The column 6, according to this third preferred embodiment, comprises a front member 24 made from a carrier made of diatomaceous earth coated with polyethylene glycol as liquids having an OH-group, a middle member 34 made from a carrier made of diatomaceous earth coated with silicon family liquids having a small polarity and a rear member 15 made from porous beads as adsorbers arranged in the order described from the upstream side to the downstream side. Although the front member 24, middle member 34 and rear member 15 constructing the column 6 are independently shown in this third preferred embodiment, respectively, they can be arranged side by side in one piece of column pipe.

Accordingly, when the sample gas is introduced into the column 6 from the side of the front member 24 with the carrier gas, alcohols ($CH_3OH$, $C_2H_5OH$ and the like) and the aromatic hydrocarbons ($C_6H_6$, $C_7H_8$ and the like) contained in the sample gas are adsorbed by the front member 24 while other components flow to the downstream side. Thus, the high-boiling-point aliphatic hydrocarbons are adsorbed by the middle member 34 while other components flow to the rear member 15, so that the low-boiling-point hydrocarbons are adsorbed by the rear member 15 while other components, such as methane and oxygen, are eluted to be flowed to the downstream side. As described above, the respective components of the nonmethane hydrocarbons contained in the sample gas are separately adsorbed by the front member 24, the middle member 34 and the rear member 15 constructing the column 6, respectively. Accordingly, when the carrier gas is backflushed from the side of the rear member 15 to the side of the front member 24, the respective components adsorbed by the front member 24, the middle member 34 and the rear member 15, respectively, can be smoothly eluted and thus the respective components can be measured at high speed with reducing the tailing.

As first described in the second preferred embodiment, the front member of the column is made from the carrier coated with the liquids having an OH-group, so that both the high-boiling-point hydrocarbons and the components having an OH-group and thus high in polarity can be adsorbed by the front member, and the low-boiling-point hydrocarbons other than methane can be adsorbed by the rear member arranged on the downstream side of this front member. Accordingly, when the carrier gas is backflushed from the side of the rear member to the side of the front member, not only can the high-boiling-point hydrocarbons and the components, such as alcohols, be comparatively easily and rapidly eluted from the front member to be introduced into the detector at high speed as they are, but also the low-boiling-point hydrocarbons can be comparatively quickly eluted from the rear member to be transferred to the detector. Thus, the nonmethane hydrocarbons adsorbed by the front member and the rear member of the column can be accurately measured at high speed as one peak with reducing the tailing.

Next, in the above-described third preferred embodiment, the middle member made from the carrier coated with the silicon family liquids is arranged between the front member and the rear member to construct the column, so that the high-boiling-point aliphatic hydrocarbons eluted from the front member can be adsorbed by the middle member. Accordingly, also in the case where alcohols and the high-boiling-point aliphatic hydrocarbons are contained in the sample gas, those respective components are adsorbed by the front member and the middle member, respectively, and the low-boiling-point hydrocarbons other than methane are separately adsorbed by the rear member. Thus, when the carrier gas is backflushed, the above-described respective components can be smoothly eluted, so that the respective components can be measured in high speed with reduced tailing.

What is claimed is:

1. A hydrocarbon analyzer for rapidly detecting and measuring hydrocarbon components of a gas sample, said analyzer comprising:
    means for separately adsorbing methane and nonmethane hydrocarbon components of said gas sample;
    means for introducing said gas sample with a carrier gas from a carrier gas line into said means for separately adsorbing;
    a branched line severably connected between said carrier gas line and a first flame ionization detector for measuring said nonmethane hydrocarbon components of said gas sample;
    a second flame ionization detector for measuring said methane components of said gas sample, said second flame ionization detector connected to said means for separately adsorbing; and
    a change-over valve for switching said means for separately adsorbing, said means for introducing, said branched line, and said first and second flame ionization detectors from a gas sample introducing position to a backflush position.

2. The analyzer of claim 1 wherein said means for separately adsorbing further comprises a nonmethane hydrocarbon adsorbing first column connected in series with a methane adsorbing second column.

3. The analyzer of claim 2 wherein said means for introducing said gas sample includes a sample gas measuring pipe from which said sample gas is propelled by said carrier gas into the upstream end of said first column and through to the downstream end of said second column.

4. The analyzer of claim 3 wherein said branched line extends from said carrier gas line upstream of said sample gas measuring pipe and terminates through a bypass line into said first flame ionization detector when said change-over valve is in said gas sample introducing position.

5. The analyzer of claim 4 wherein said second flame ionization detector is connected to the downstream end of said methane adsorbing second column.

6. The analyzer of claim 5 wherein said change-over valve in its backflush position simultaneously disconnects said sample gas measuring pipe from the upstream end of said nonmethane adsorbing first column, disconnects said first column from the upstream end of said methane adsorbing second column, connects said carrier gas line to the downstream end of said first column, disconnects said bypass line from said branched line, connects the upstream end of said first column to said first flame ionization detector via said bypass line to backflush said first column, and connects said branched line to the upstream end of said methane adsorbing second column.

7. The analyzer of claim 2, wherein said nonmethane hydrocarbon adsorbing first column comprises a front member for adsorbing high-boiling-point hydrocarbons and a rear member for adsorbing low-boiling-point hydrocarbons.

8. A hydrocarbon analyzer for rapidly detecting and measuring high polarity nonmethane components and high-boiling-point and low-boiling-point nonmethane components of a gas sample, said analyzer comprising:
    a nonmethane adsorbing column having an upstream end, a downstream end, a front member disposed on said upstream end and including a carrier coated with liquids having an OH-group to adsorb said high polarity and high-boiling-point components, and a rear member disposed on said downstream end and including adsorbers for adsorbing low-boiling-point components;
    means for introducing said gas sample in a carrier gas from a carrier gas line from a sample gas measuring pipe into said upstream end of said column;
    a branched line extending from said carrier gas line upstream of said sample gas measuring pipe and including a bypass line terminating into a flame ionization detector; and
    a change-over valve for switching from an initial gas sample introducing position connecting said carrier gas line, said sample gas measuring pipe and said adsorbing column simultaneously in parallel with said branched line, said bypass line and said flame ionization detector, to a backflush position, simultaneously disconnecting said measuring pipe from said column, connecting said carrier gas line to said downstream end of said column, and connecting said upstream end of said column to said flame ionization detector to backflush said column.

9. The analyzer of claim 8, wherein said rear member is disposed parallel to said front member within said column.

10. The analyzer of claim 8, wherein said column comprises:
    a front member disposed on said upstream end within said column and including a carrier coated with liquid having an OH-group to adsorb high polarity components;
    a middle member disposed within said column for adsorbing said high-boiling-point components; and a rear member disposed within said column on said downstream end of said column for adsorbing said low-boiling-point components.

11. The analyzer of claim 10, wherein said front, middle and rear members are disposed mutually parallel within said column.

12. The analyzer of claim 8, further comprising a second column for separating components other than nonmethane hydrocarbons severably connected through said change-over valve between said downstream end of said column and said flame ionization detector.

13. The analyzer of claim 8, wherein said front member comprises diatomaceous earth or fluororesin coated with polyethylene glycol and said rear member comprises porous polymeric beads.

14. The analyzer of claim 13, wherein said porous polymeric beads are coated with a low vapor pressure, thermally stable hydrocarbon grease.

15. The analyzer of claim 10, wherein said middle member comprises diatomaceous earth coated with silicone liquid.

16. A method of detecting and measuring methane and nonmethane hydrocarbons in a sample gas, said method comprising the steps of:
  introducing a sample gas into the sample gas measuring pipe of the hydrocarbon analyzer of claim 2;
  setting said change-over valve to an initial position simultaneously connecting said measuring pipe, first column, second column, and second flame ionization detector in series with and downstream of said carrier gas line, and connecting said branched line from said carrier gas line in series with said bypass line to said first flame ionization detector;
  activating said carrier gas line to flow said sample gas in said measuring pipe through said first and said second columns to adsorb any nonmethane hydrocarbons in said first column and elute methane into said second column for separation and subsequent detection by said second flame ionization detector;
  switching said change-over valve to a backflush position disconnecting said measuring pipe from said carrier gas line and simultaneously connecting said carrier gas line to said downstream end of said first column, connecting said upstream end of said first column via said bypass line to said first flame ionization detector, and connecting said branched line from said carrier gas line in series with said second column to said second flame ionization detector; and
  activating said carrier gas line to backflush said first column, eluting any nonmethane hydrocarbons therein into said first flame ionization detector and any methane from said second column into said second flame ionization detector.

17. A method of detecting and measuring nonmethane hydrocarbons in a sample gas, said method comprising the steps of:
  introducing a sample gas into the sample gas measuring pipe of the hydrocarbon analyzer of claim 8;
  setting said change-over valve to said initial position and activating said carrier gas line to introduce the contents of said measuring pipe into said front member of said column to adsorb high polarity and high-boiling-point hydrocarbons, and then into said rear member of said column to adsorb low-boiling-point hydrocarbons other than methane; and
  switching said change-over valve to said backflush position and activating said carrier gas line, to elute and transfer said high-boiling-point hydrocarbons adsorbed by said front member and said low-boiling-point hydrocarbons adsorbed by said rear member via said bypass line to said flame ionization detector.

18. The method of claim 17 further comprising the additional steps of:
  interposing a second column for separating components other than nonmethane hydrocarbons between said nonmethane adsorbing column and said flame ionization detector; and
  bypassing said second column to establish an uninterrupted path for elution of said nonmethane components into said flame ionization detector when said change-over valve is in said backflush position.

* * * * *